United States Patent [19]

Nozaka et al.

[11] Patent Number: 5,030,833
[45] Date of Patent: Jul. 9, 1991

[54] METHOD AND DEVICE FOR DETECTING OBJECTS CONTAINING FLUORESCENT SUBSTANCES

[75] Inventors: Yoshiki Nozaka, Setagaya; Tetsuro Katsuta, Asaka; Masahiko Chiba, Shibuya; Hiroshi Miyama, Kita, all of Japan

[73] Assignee: Dai Nippon Insatsu Kabushiki Kaisha, Japan

[21] Appl. No.: 254,655

[22] PCT Filed: Feb. 5, 1988

[86] PCT No.: PCT/JP88/00109
§ 371 Date: Sep. 28, 1988
§ 102(e) Date: Sep. 28, 1988

[87] PCT Pub. No.: WO88/05909
PCT Pub. Date: Aug. 11, 1988

[30] Foreign Application Priority Data

Feb. 6, 1987 [JP] Japan ................................. 62-26105
Apr. 15, 1987 [JP] Japan ................................. 62-92632
Apr. 22, 1987 [JP] Japan ................................. 62-99304

[51] Int. Cl.$^5$ ............................................. G01N 21/64
[52] U.S. Cl. ................................. 250/461.1; 250/459.1
[58] Field of Search .............. 250/461.1, 459.1, 458.1, 250/372, 302

[56] References Cited

U.S. PATENT DOCUMENTS 3,956,630 5/1976 Mellows ............................. 250/302
4,778,999 10/1988 Fisher ............................. 250/461.1

FOREIGN PATENT DOCUMENTS 55-143553 4/1980 Japan.

Primary Examiner—Jack I. Berman
Assistant Examiner—Richard Hanig
Attorney, Agent, or Firm—Parkhurst, Wendel & Rossi

[57] ABSTRACT

An ultraviolet beam from an ultraviolet radiation source is projected to an object having a fluorescent substance such as an adhesive-applied position on a continuous sheet of paper which is being transported and the luminous emission from the fluorescent substance is detected by light reception elements in a detection unit. In this case, at least more than two light reception elements are provided and the arithmetic process of the value of the output from each of the light reception elements is executed by a control computer disposed in a device main body. The value thus obtained is compared with a comparison value stored in storage means, thereby detecting the failure or the degree of adhesive application. When the failure of adhesive application is detected, an alarm buzzer is actuated while a lamp is turned on.

The invention is therefore utilized for the inspection of portions to which an adhesive is applied in the adhesive application step carried out by collators, box-making machines, book-binding machines or the like.

10 Claims, 9 Drawing Sheets

METHOD AND DEVICE FOR DETECTING OBJECTS CONTAINING FLUORESCENT SUBSTANCES

TECHNICAL FIELD

The present invention relates to a method and device for detecting objects containing fluorescent substances, and more particularly, an adhesive-application detection method and device for not only detecting the failure of adhesive application or the state of adhesive application, but also controlling the quantity of adhesive to be applied by the fluorescent emission in the adhesive application process in devices such as collators, box-making machines, book-binding machines or the like.

BACKGROUND ART

So far as one of the methods used for detecting the presence or absence of objects to be detected, the quantities and positions thereof, there has been a method for irradiating ultraviolet rays to an object to be detected, to which is glued a fluorescent substance or to which is applied or added a fluorescent agent for which the luminous emission from the fluorescent substance or agent is detected by a photosensor. However, the intensity of luminous emission from a fluorescent substance is fundamentally very weak, such that in order to improve the detection rate, a sensor, an ultraviolet-ray source and a work must be surrounded by light-shielding plates or boxes so as to eliminate adverse effects due to external light rays or the like. Consequently, there exists the defect that special boxes or the like must be provided, and thus, the range of utilization is considerably limited. Therefore, in order to improve the above-mentioned method, there has been proposed a method for disposing an optical filter with a narrow transmission wavelength band in front of a photosensor so as to selectively detect only the luminous emission from a fluorescent substance. However, according to this method, the luminous emission from the fluorescent substance for which the intensity is fundamentally considerably weak, is received through a filter with a low degree of transmissivity so that the output signal from the photosensor is further decreased in strength. As a consequence, there arises the defect that not only does the amplifier circuit in the succeeding stage become complex in construction, but also a reduction in the S/N ratio results. In addition, in order to process the above-mentioned signal, an expensive device of complex construction is needed. As described above, there has not been available so far a method capable of detecting a fluorescent substance in an inexpensive and simple manner, and consequently, visual inspection is presently employed in practice. However, according to the latter method, a person must continue a simple task for a long period of time and furthermore, must continuously observe the weak light in a dark place. Thus, there arise the problems of the production efficiency being considerably low; resultant individual differences; and the method not being safeguarded against health hazards.

Furthermore, in order to detect the failure and state of adhesive application in the adhesive application process for devices such as collators, box-making machines and book-binding machines or the like, a photosensor has been utilized in such a way that light is projected on an applied paste and the light reflected therefrom or transmitted therethrough is intercepted by the photosensor, whereby the quantity of applied paste or whether or not the applied paste exists, is detected in response to the variations in the light-reception signals output from the photosensor. However, according to this method, whether or not a paste exits is detected in response to the intensity of the reflected or transmitted light which is received, requiring that a light beam with a predetermined intensity must be projected at an object to be detected, while maintaining a predetermined distance and angular relationship between an object to be detected and the photosensor. In addition, objects to be detected or the color and composition of an object to be compared must be maintained uniform. For instance, in the case of collators, in most cases an adhesive is applied at the width of 1 mm and the light beam with a predetermined intensity must be projected at the applied paste which is fine in shape and small in quantity so that extremely delicate setting conditions are required. As a result, the above-mentioned detection method has a defect that the degree of operability is considerably worse. There exists the further problem that sheets of paper or film which are to be applied with an adhesive have been already printed, so that decolorization inevitably results.

In view of the above, there has been proposed a method which takes into consideration the water content in a paste or adhesive so that the detection of the quantity of applied adhesive or the detection whether or not there exists an applied adhesive is made in response to the difference in electrostatic capacitance between sheets of paper or film due to the difference in water content therein. However, when there exists a piece of metal in the vicinity of an electrostatic-capacitance sensor, this measurement becomes impossible. Furthermore, in order to measure the difference in extremely low electrostatic capacitance, the fine position arrangement of a probe must be made. This method has a shortcoming that the measurement is easily and adversely affected by vibration of an object to be measured. Thus, this method has the defects of worsened operability and adversely affected production to a remarkable degree.

As described above, the conventional detection methods are unsatisfactory in practice so that at present, an inspector makes a visual or sampling inspection or he/she makes a total or 100% inspection in another step so as to detect the failure of adhesive application. However, it is physically impossible to completely eliminate the objects which must be rejected by the visual or sampling inspection, and differences in the results of inspection between individual inspectors occur. Furthermore, however highly improved the performance of a device is, the workers have not been completely freed from the inspection processes. And moreover, even when the total or 100% inspection is made by a worker in another step, he/she must continue a simple task for a long period of time, so that there arises the problem that the production efficiency is considerably degraded.

In addition, in order to improve the qualities of products, the quantity of applied adhesive, and whether or not there exists an applied adhesive, must be accurately and properly detected so that the quantity of applied adhesive is controlled to a predetermined value, whereby the products to be rejected can be fundamentally eliminated.

DISCLOSURE OF THE INVENTION

Objects

In view of the above, the present invention was made and has for its object, to provide a method for detecting objects by use of a fluorescent substance by a plurality of photosensors which detect an object applied with a fluorescent substance so that the object can be detected with a high S/N ratio. Thus, the automation of the inspection process can be realized and the production efficiency can be improved.

Another object of the present invention is to provide an adhesive application method and a device for automatically applying an adhesive to sheets such as continuous sheets or sheets of film so as to accomplish a desired process, which can detect the failure of adhesive application or the quantity of applied adhesive in response to the degree of the luminous emission from an added fluorescent substance. Thus, the automation of the inspection step can be realized and the production efficiency can be improved.

A further object of the present invention is to provide a device for controlling the quantity of adhesive to be applied for a device of the type for automatically applying an adhesive to sheets such as continuous sheets or sheets of film. A desired process is thereby accomplished, which detects the quantity of adhesive applied in response to the degree of luminous emission from a fluorescent substance added, and control so as to maintain the applied quantity of adhesive at a predetermined value by feedback so that automation of the inspection step can be realized. Thus, the failure of adhesive application is eliminated completely, enabling the production efficiency to be improved.

Means for Attaining the Objects

In order to attain the above-mentioned objects, according to the present invention, the ultraviolet beam is projected at an object having a fluorescent substance. The detection by the fluorescent substance is made by photosensors for detecting the luminous emission from the fluorescent substance. At least more than two photosensors are provided. The output value from each photosensor is subjected to a subtraction process so that the object can be detected without being adversely affected by external light disturbances, changes in color and quality of the object to be detected, etc.

In the devices for automatically applying an adhesive to sheets or the like which are being transported, thereby accomplishing a desired process, the objects can be attained by previously adding a fluorescent substance to the adhesive. Additionally, in the step in which the adhesive added with the fluorescent substance is applied to the sheets or the like, the objects can be attained by projecting the ultraviolet beam at the adhesive and detecting the luminous emission therefrom by more than two photosensors, thereby detecting the failure of adhesive application. Another invention relates to an adhesiveapplication detection device for a device of the type for applying an adhesive to sheets which are being transported and to which a fluorescent substance has been previously added to the adhesive, thereby accomplishing a desired process. The abovementioned objects of the present invention can be attained by the following: the provision of means for projecting the ultraviolet beam to the adhesive in the step in which the adhesive is applied to the sheets which are being transported; light source means for projecting the ultraviolet beam to the adhesive; detection means comprising more than two photosensors for detecting the degree of the luminous emission from the adhesive caused by the irradiation of the beam from the light source means means for detecting whether or not the failure of adhesive application resulted in a response to the detected signal from the detection means, and generating a failure alarm in the case of a predetermined existing state.

Furthermore, in the cases of the devices of the type for automatically applying an adhesive to sheets or the like which are being transported and the adhesiveapplication-quantity control devices for adhesive application or coating devices of the type for accomplishing the adhesive application process by the use of the adhesive previously added with a fluorescent substance, the above-mentioned objects of the present invention can be attained by the following: the provision of a light source for projecting the ultraviolet beam at the adhesive in the step in which the adhesive is applied to the sheets or the like which are being transported; detection means for detecting the degree of the luminous emission from the adhesive caused by the projection of the beam from the light source means; means for controlling the quantity of adhesive to be applied sequentially in response to the detection of the quantity of adhesive applied to the sheets or the like; and adhesive application or coating means for applying the adhesive to the sheets or the like in response to the control data.

Mode of Operation

According to the present invention, the ultraviolet beam is projected at an object having a fluorescent substance; the luminous emission from the fluorescent substance as well as external disturbance light are intercepted by a plurality of photosensors such as photodiodes or the like, and the output data are processed by an arithmetic circuit so that the object can be detected with a high S/N ratio (even when external light disturbance exists).

In the case of the adhesive application process for collators, box-making machines, book-binding machines or the like, according to the present invention, a fluorescent substance is added beforehand to an adhesive to be used in a process, the ultraviolet beam is projected from an ultraviolet beam source such as blacklight or the like to the adhesive, and the degree of the luminous emission therefrom is detected as the quantity of adhesive applied. Thus, the failure of adhesive application or whether or not the adhesive exists can be automatically detected.

Furthermore, in the process of adhesive application by the adhesive application or coating devices for collators, box-making machines, book-binding machines or the like, according to the present invention, an adhesive to be used in the process has a fluorescent substance added beforehand. In the step of applying the adhesive with the fluorescent substance added to sheets such as continuous sheets or sheets of film which are being transported at the adhesive application station, the ultraviolet beam is projected from an ultraviolet beam source such as black-light or the like to the adhesive. The degree of the luminous emission therefrom is detected as the quantity of adhesive applied and processed by a computer within a device main body so as to input the data into the adhesive application station by a feedback system, whereby the adhesive applied can be maintained at a predetermined quantity.

Effects

According to the present invention, a method for detecting objects by use of a fluorescent substance which can detect an object with a high S/N ratio to realize automation of the inspection step and can improve the production efficiency, can be provided. For instance, the efficient detection of applied adhesive without accompanying adverse effects due to external light disturbance and the like, can be realized so that the automatic total or 100% inspection can be carried out to check the failure of adhesive application or to measure the quantity of adhesive applied simultaneously with the adhesive application step. As a result, high-quality products can be maintained and productivity can be improved. Furthermore, the device according to the present invention accomplishes the accurate inspection hitherto made by man, so that the workers are freed from the monotonous inspection process; the total or 100% inspection in another step can be eliminated and savings in energy and manpower can be facilitated remarkably.

Furthermore, according to the present invention, the quantity of adhesive applied to sheets or the like can be maintained uniform by a feedback system so that high-quality products can be ensured while eliminating products to be rejected, and improving productivity.

DETAILED DESCRIPTION OF THE PREFERRED EMBODIMENTS

Figure 1:
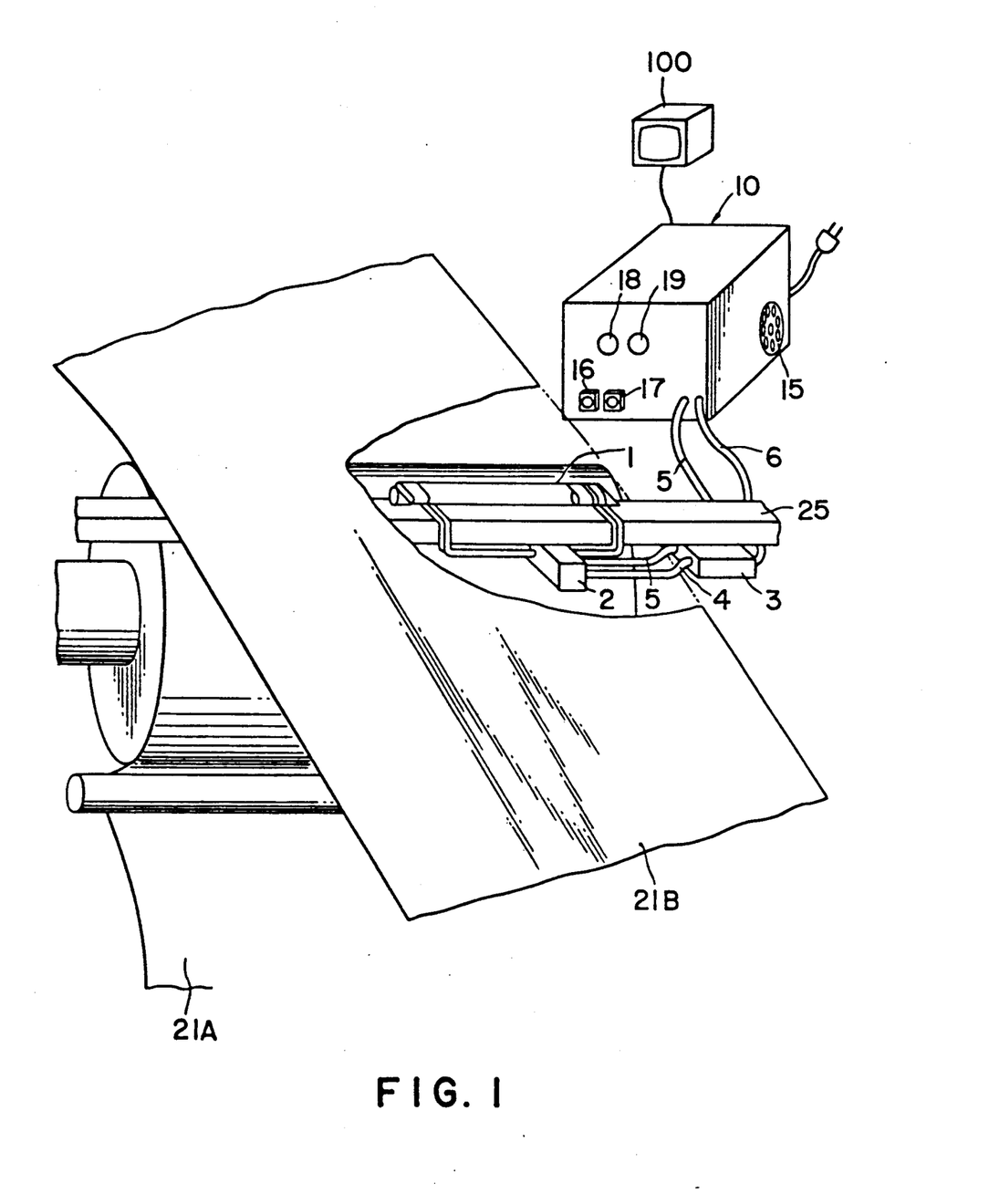
FIG. 1 is a view illustrating a device for detecting the failure of adhesive application which embodies a method of the present invention and is used for a collator.

FIG. 1 shows a device for detecting the failure of adhesive application which carries out a method in accordance with the present invention for detecting objects to be detected by the use of a fluorescent substance, and which is used in a collator. A device for detecting the failure of adhesive application (which is referred to as "the adhesive-application-failure detection device" hereinafter in this specification), comprises an ultraviolet radiation source 1, a detection unit 2 and an analog-signal amplifier 3, all of which are mounted on a supporting member 25 of a collator and a device main body 10. All component units of the device are interconnected to each other through signal lines 4 and 5 and a power source line 6, so that the failure and the quantity of an adhesive applied to continuous sheets 21A and 21B which are being transported can be detected. The front panel of the device main body 10 is provided with a power source switch 16, a reset switch 17, a lamp 18 which is turned on in the case of the satisfactory adhesive application, a lamp 19 which is turned on in the case of the failure of adhesive application, and a display 100 for the display of the quantity of the adhesive. One side panel of the device main body 10 is provided with an alarm buzzer for generating an alarm sound in the case of the failure of adhesive application.

Figure 2:
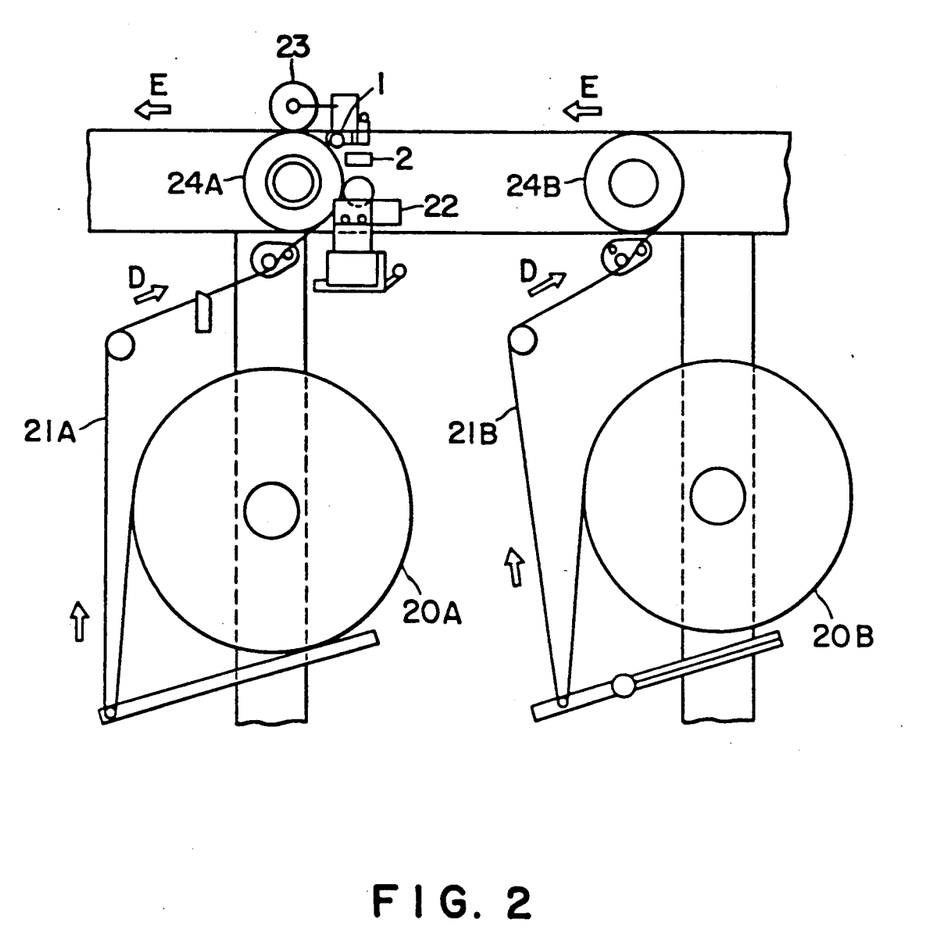
FIG. 2 is a diagram illustrating the positional relationship between an ultraviolet light source and a detection unit thereof.

FIG. 2 shows the positional relationships of the ultraviolet radiation source 1 and the detection unit 2 with respect to the collator. Rolls 20A and 20B for winding the continuous sheets 21A and 21B, respectively, are disposed below the collator in such a way that the continuous sheets 21A and 21B which are unrolled in the directions indicated by the arrows from the rolls 20A and 20B, are transported in the direction indicated by the arrows E through pin wheels 24A and 24B disposed above of rolls 20A and 20B. An adhesive application or coating device 22 is disposed in the vicinity of the pin wheel 24A in order to apply the adhesive to the continuous sheet 21A which is being transported and a spring wheel 23 is disposed upwardly of the pin wheel 24A for forcing the continuous sheets 21A and 21B, which are being transported, to press against each other so as to join them. The detection unit 2 is disposed upwardly of the adhesive application or coating device 22 and the ultraviolet radiation source 1, which is disposed above the detection unit 2, projects the ultraviolet beam BL to the adhesive in the step of the application of the adhesive to the continuous sheet 21A which is being transported in the direction indicated by the arrows E through the pin wheel 24A. The detection unit 2 is adapted to efficiently detect only the luminous emission from the adhesive and external disturbance light rays KL1 and KL2.

Figure 3:
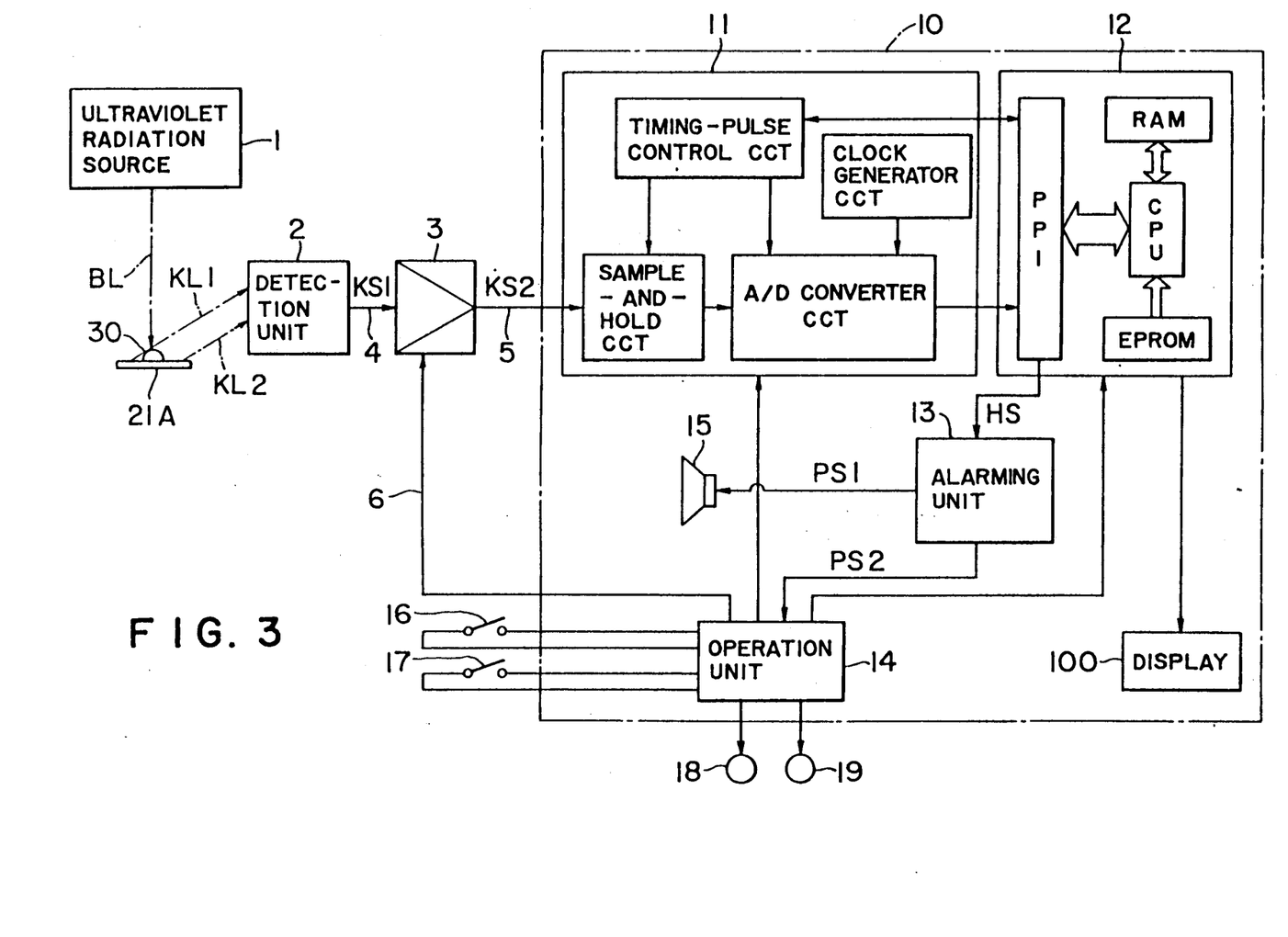
FIG. 3 is a block diagram illustrating the construction of the circuit system of the device for detecting the failure of adhesive application.

FIG. 3 shows in block diagram the construction of the circuit system of the adhesive application or coating detection device which will be described in detail below.

(1) Ultraviolet Radiation Source 1

A fluorescent-lamp type black light or the like is used as the ultraviolet radiation source 1 which projects the ultraviolet beam BL to the adhesive 30 (previously added with a fluorescent substance) applied to the continuous sheet 21A which is being transported. In order not only to maintain the intensity of the ultraviolet radiation at a predetermined level in terms of time but also to stabilize the luminous emission from the adhesive 30, the fluorescent-lamp type black light is turned on at a high frequency by using a high-frequency power supply (of the order of 20 KHz). The ultraviolet radiation source 1 and the detection unit 2 are so arranged that the light reception face of the detection unit 2 makes an angle of 45° with respect to the ultraviolet radiation source 1, thereby reducing the incidence efficiency of the ultraviolet beam BL emitted from the ultraviolet radiation source 1, incident directly on the light reception face of the detection unit 2 and consequently improving the S/N ratio. The following countermeasure is employed against the variation in light quantity (degradation) from the ultraviolet radiation source. Namely, when the quantity of adhesive is preset in accordance with the experience of an operator, there arises the problem of the variation in light quantity. In order to eliminate the adverse effect due to the variation in light quantity of the ultraviolet radiation source, a mechanism for measuring the intensity of the ultraviolet beam is therefore independently arranged at a sensor head unit so that the luminous-emission signal representative of the quantity of adhesive is divided by the intensity of the ultraviolet beam, thereby normalizing the signal. This value is compared with reference data corresponding to variations in light quantity.

(2) Detection Unit 2

Figure 4:
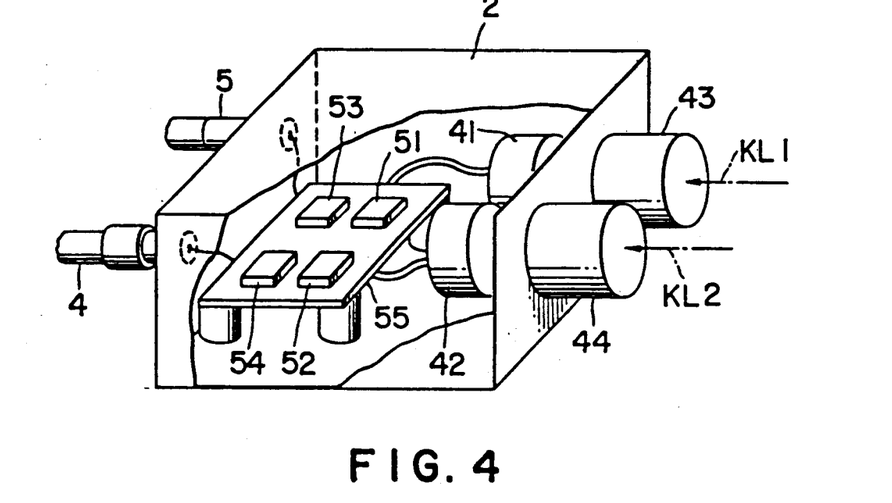
FIG. 4 shows the construction of the detection unit.

The detection unit 2 has the construction as shown in FIG. 4. The luminous emission and the external disturbance light rays KL1 and KL2 received through light-reception feeds 43 and 44 are converted into electrical signals which in turn are processed in such a way that they are transmitted as a detection signal KS1 through the signal line 4 to the device main body 10. Used in the interior of the detection unit 2 are photodiodes 41 and 42 each having a measuring wavelength range to respond to visible light which receive the luminous emission from the adhesive excited by the ultraviolet radiation source 1 as well as the external disturbance light rays KL1 and KL2, and which effect the photoelectric conversion. To this end, the output polarities of the photodiodes 41 and 42 are reversed. The photodiodes having the characteristic of a wide measurement field of view are used and the measurement field of view can be set in a simple manner by selecting the shape of the light reception unit or the lens system.

Figure 5:
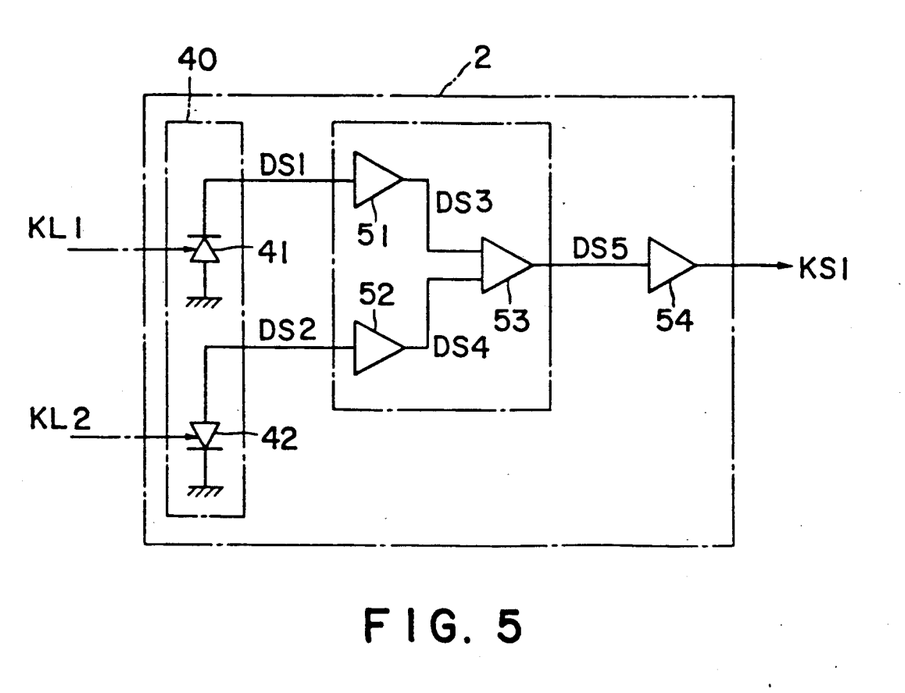
FIG. 5 is a circuit diagram thereof.

The outputs from the photodiodes 41 and 42 are input through lines into a substrate 55. Three operational amplifiers 51, 52 and 53, each consisting of an IC and an amplifier 54 are mounted on the substrate 55. The detection unit 2 of the type described above, has the circuit construction as shown in FIG. 5, comprising photodiodes 41 and 42 constituting a light-reception unit 40, operational amplifiers 51–53, and an arithmetic circuit unit 50. Light-reception signals DS1 and DS2 which are opposite in polarity with respect to each other, and from the photodiodes 41 and 42 in the light-reception unit 40, are input into the operational amplifiers 51 and 52 in the arithmetic circuit unit 50, and the arithmetic signals DS3 and DS4 from the operational amplifiers 51 and 52 are input to the operational amplifier 53 so that the fluorescent signals DS5 representative of the difference between the two received light-reception signals DS1 and DS2 or the degree of the luminous emission from the adhesive is input to the amplifier 54, which in turn outputs the detection signal KS1. That is, in the detection unit 2, the signal levels of the arithmetic signals DS3 and DS4 from the two photodiodes 41 and 42 are subtracted to generate the fluorescent signal DS5, whereby the adverse effects due to the external disturbance light rays can be eliminated and the S/N ratio can be improved without causing a decrease in the intensity of the luminous emission received from the fluorescent substance.

(3) Analog-Signal Amplifier 3

The analog-signal amplifier 3 comprises two operational amplifiers such as MOS type input operational amplifiers, and is adapted to output to the succeeding stage circuit the detection signal KS1 obtained by the light reception and the photoelectric conversion in the detection unit 2 after the detection signal KS1 is made to be easily detected and its S/N ratio is improved.

(4) Device Main Body 10

(a) Decision Unit (1) A/D Conversion Unit 11

The A/D conversion unit 11 comprises a timing-pulse control circuit, a clock generator circuit, a sample-and-hold circuit, an A/D converter circuit and the like, and is adapted to convert to sample the detection signal KS2 from the analog-signal amplifier 3, and convert it into the digital signal, which in turn is input to a one-board control computer 12. The timing-pulse control circuit determines the time required for the A/D conversion in such a way that the clock pulses which are generated at a predetermined period by the clock generator circuit and control the operation timing of the sample-and-hold circuit and the A/D conversion circuit in response to the control pulse transmitted from the one-board control computer 12, are clock-input to the A/D conversion circuit. In order to eliminate the conversion error resulting from A/D conversion, the sample-and-hold circuit samples the analog voltage during the A/D conversion and maintains it at a data value at this time. In this case, sampling is carried out at a frequency of the order of 1–10 KHz. A commercially available 8- or 10-bit sequential conversion type A/D conversion IC or the like is used as the A/D conversion circuit. The input side is of the bipolar input type and the range of the input signal is widened so that the whole circuit can be simplified in construction. Furthermore, buffers for individual bits are incorporated in the output side so as to counter the effects of noise.

(2) Control computer 12

The control computer 12 is a one-board computer comprising a central processing unit (CPU), storage devices (RAM, EPROM), an input-output interface (PPI), a decoder, a timer and the like. The signal intensity representative of a product to be rejected is determined in response to two values of the intensity of the signal input from the preceding stage circuit through the input-output interface when the adhesive application is completely satisfactory, and the intensity of the signal also input from the preceding stage through the input-output interface when the adhesive is not applied at all, and the value thus obtained is stored in a storage device as a comparative value. In particular, in order to eliminate the differences between the individual workers, the data for controlling the quantity of adhesive for each kind of product are prepared on the basis of experience, thereby constructing a system for presetting an optimum quantity of adhesive. In this case, OK values and alarm levels in excess thereof are determined for the values of the signals representing excessive and insufficient adhesive application, thereby controlling the adhesive application condition. Thereafter, the values of the input signals sequentially read out from the input-output interface are compared with the decision value stored in the storage device in the central processing unit, thereby determining whether or not there exists the failure of adhesive application or the degree of adhesive application. When a failure of adhesive application is detected, the central processing unit calculates the comparison signal HS which in turn is input through the input-output interface into an alarm device 13. Furthermore, the (digital) value corresponding to a predetermined quantity of adhesive is previously stored in a storage device and the input signal read out in the manner described above is detected and displayed on the display 100.

(3) Alarm Device 13

The alarm device 13 comprises a sequence of relays, generates the control signal PS1 for actuating the alarm buzzer 15 in response to the decision signals HS from the control computer 12 and inputs into an operation unit 14 the control signal PS2 for turning on the lamp 19.

(b) Operation Unit 14

The operation unit 14 comprises a power switch 16, a reset switch 17 and lamps 18 and 19. An operator actuates the adhesive-application-failure detection device and further confirms the adhesive application condition and when a failure of adhesive application occurs, the device main body 10 is reset and returned to the mode capable of further detection. When the detection device is used, the operator depresses the power switch 16 and then the reset switch 17 after countermeasures against the failure of adhesive application have been implemented in response to the detection of the failure of adhesive application. The mode of operation of the adhesive-application-failure detection device with the above-described construction which is used in a collator will be described.

First, the adhesive-application-failure detection device is set into the collator as shown in FIG. 1 and the adhesive 30 to which a fluorescent substance has been added beforehand, is fed into the adhesive application or coating device 22. Thereafter, the operator depresses the power switch 16 on the device main body 10 when the collator is activated, thereby activating the adhesive-application-failure detection device. The adhesive 30 is applied by the adhesive application or coating device 22 to the continuous sheet 21A unrolled from the roll 20A and the luminous emission from the fluorescent substance in the adhesive 30 excited by the ultraviolet radiation source 1 and the external disturbance light rays KL1 and KL2 are detected by the detection unit 2. The output is input through the analog-signal amplifier 3 into the device main body 10 and is processed by the D/A conversion unit 11, the control computer 12 and the alarm device 13 so that when the adhesive application is satisfactory, the lamp 18 of the operation unit 14 is turned on. When failure of the application of the adhesive to the continuous sheet 21A is detected by the detection unit 2, not only the sound is generated by the alarm buzzer 15 of the device main body 10 but also the lamp 19 in the operation unit 14 is turned on, thereby giving the alarm to the operator. Then, the operator deactivates the collator and after he/she has checked the failure of the application of the adhesive to the continuous sheets 21A and 21B, he/she depresses the reset switch 17 in the operation unit, thereby resetting the device main body 10 and activating the collator again. The adhesive-application-failure detection device causes the display of the quantity of adhesive by the display 100 so that the operator can check the quantity of adhesive and control the quality of the adhesive application.

In this case, the quantity of the fluorescent substance contained in the adhesive is such that a 1–5% aqueous solution is added at a ratio of from 0.3 to 10% and in this embodiment, a 4% aqueous solution is added at the ratio of 1%. An automatic weighing and feeding device capable of feeding a predetermined quantity of adhesive in one shot can be used in the case of adding the fluorescent substance to the adhesive. In order to uniformly mix the adhesive with the fluorescent substance, the inside walls of a mixing chamber are coated with Teflon (the registered trademark) in order to prevent the adhesion of the adhesive. Furthermore, according to the above-described embodiment, a one-board computer is used as the control computer 12 in the device main body 10, but it is to be understood that a personal computer can also be used. The alarm buzzer 15 and the lamps 18 and 19 are used to generate the alarm to the operator, but it is to be understood that the machine can be so designed and constructed that it can be directly deactivated in response to the output signal from the alarm device 13. When a plurality of detection units 2 are detected by a single decision unit, the latter can be incorporated with a multiplexing circuit so that the detection signals can be subsequently compared. Furthermore, it is possible to arrange a plurality of adhesive-application-failure detection devices in an on-line manner so that the control of the quantity of adhesive may be unified or centralized.

Figure 6:
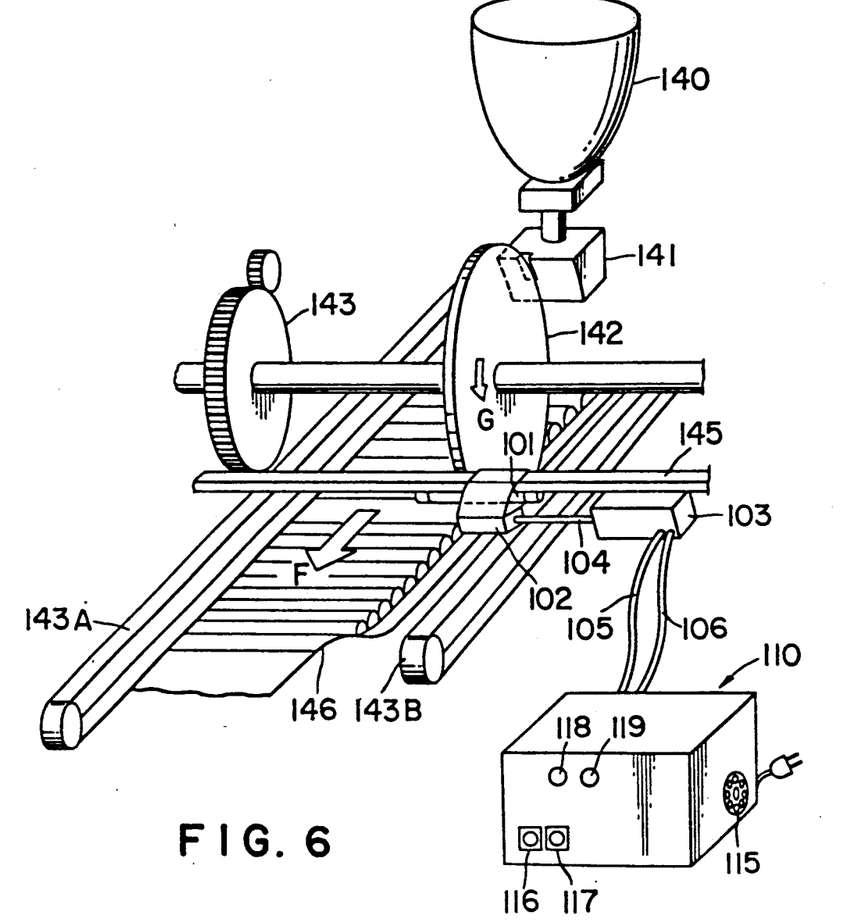
FIG. 6 is a view illustrating the device for detecting the failure of adhesive application which is used in an adhesive application or coating device of a box-making machine.

FIG. 6 shows the adhesive-application detection device in accordance with the present invention which is used in the adhesive application or coating device of a box-making machine. In the adhesive device for detecting application failures, an ultraviolet radiation source 101, a detection unit 102 and an analog-signal amplifier 103 are mounted on a supporting member 145 and are interconnected with a device main body 110 through signal lines 104 and 105 and a power cord 106, whereby the failure or the quantity of adhesive application to a developed sheet 150 transported from the box-making machine can be detected.

Figure 7:
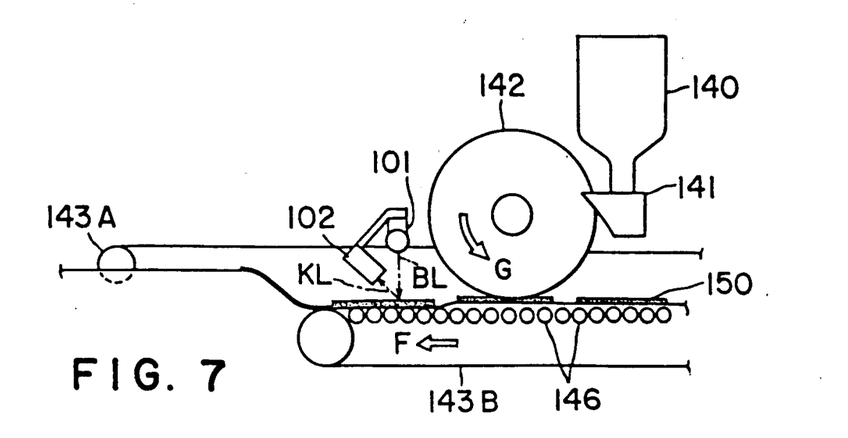
FIG. 7 shows an ultraviolet light source thereof.

FIG. 7 shows the positional relationships of the ultraviolet radiation source 101 and the detection unit 102 with respect to the adhesive application or coating device which will be described below with reference to FIG. 6. The adhesive application or coating device is provided with feed belts 143A and 143B for transporting the developed sheet 150 in the direction indicated by the arrow F on rollers 146. Disposed above the rollers 146 is an adhesive application or coating wheel 142 which is rotated in the direction indicated by the arrow G by an adhesive-application or -coating wheel driving gear 143 so that it applies the adhesive to the developed sheet 150 on the rollers 146 while rotating. An adhesive reservoir 141 for feeding the adhesive to the adhesive wheel 142 and an adhesive tank 140 for feeding the adhesive to the adhesive reservoir 141 are disposed on the right side of the adhesive wheel 142. The ultraviolet radiation source 101 and the detection unit 102 are disposed on the left side of the adhesive wheel as indicated in FIG. 7 and the ultraviolet beam BL is projected from the ultraviolet radiation source 101 to the developed sheet 150 applied with the adhesive and the detection unit 102 detects the luminous emission KL from the adhesive. Unlike the above-described collator, an object to be detected is not a continuous sheet but the developed sheet 150 so that whether or not the work of the developed sheet 150 which is to be detected is within the field of view of the detection unit 102 must be detected. To this end, the real-time detection of the velocity is made by disposing a photoelectric switch at a predetermined position in front of the detection unit 102 and by incorporating a rotary encoder (2) in a driving unit for driving the feed belts 143A and 143B. After the photoelectric switch is turned on in response to the data from (1) and (2), the on-off operation of the detection unit 102 is repeated after a delay time.

The mode of operation of the adhesive-application detection device with the above-described construction will be described.

First, the adhesive-application detection device is set into the adhesive application or coating device of the box-making machine as shown in FIG. 6 and an adhesive previously added with a fluorescent substance is stored in the adhesive tank 140. Next, the operator turns on a power switch 116 in the device main body 110 to activate the box-making machine so that the printed and developed sheet 150 is transported on the rollers 146 by the feed belts 143A and 143B. Then, the detection unit 102 is turned on and off in the manner described above and the fluorescent agent contained in the adhesive is excited so that the luminous emission KL is detected in the manner described above and then a lamp 118 of the operation unit 14 is turned on, indicating satisfactory adhesive application. When the failure of the application of the adhesive to the developed sheet 150 occurs, not only an alarm buzzer 115 but also a lamp 119 are turned on, giving the operator the alarm indicating the failure of adhesive application. The operator, therefore, deactivates the box-making machine or checks the developed sheet, etc. Thereafter, he/she depresses a reset switch 117 to reset the device main body 110, thereby re-starting the operation. As in the above-described case, quality control of adhesive application can be made by the display 100.

Next, an example of the use of the adhesive-application detection device of the type described above in the adhesive application or coating device of a book binding machine will be described.

Figure 8:
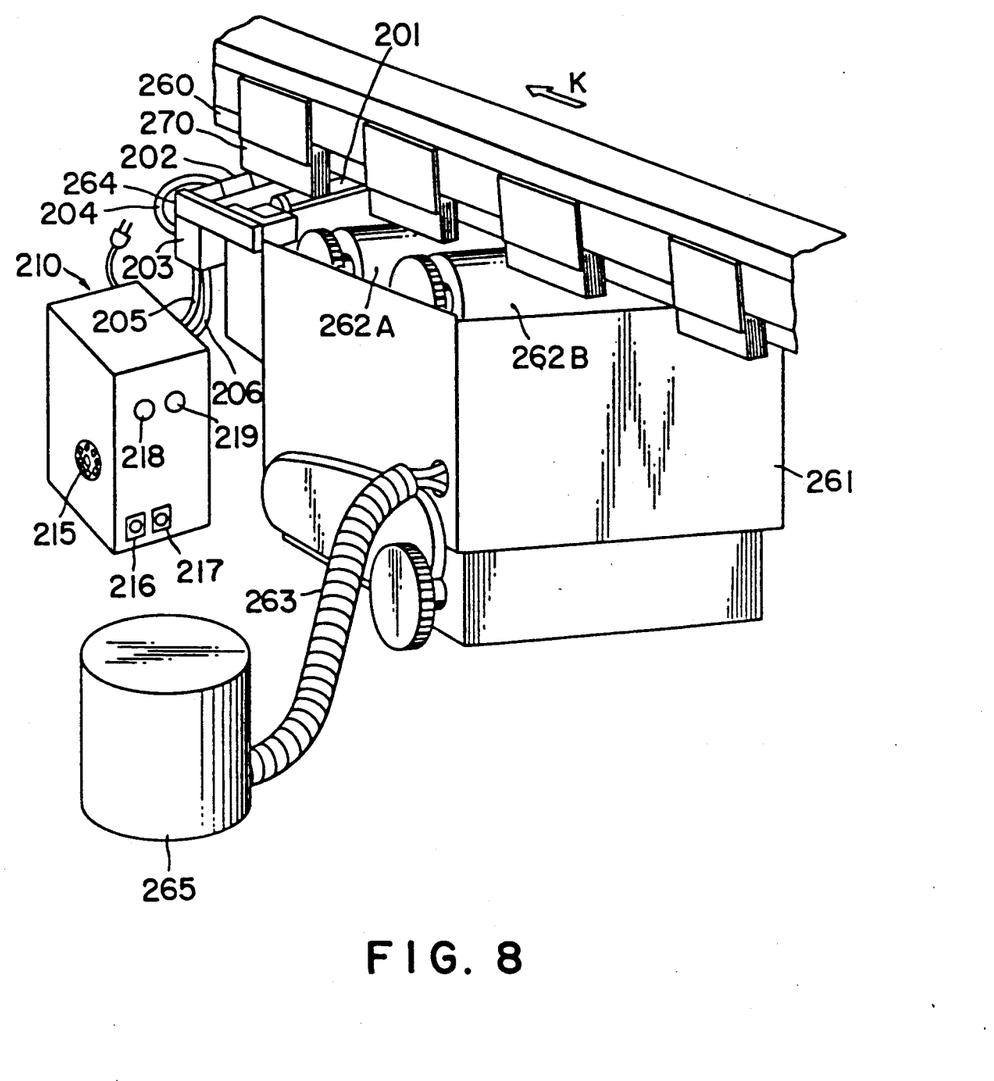
FIG. 8 is a view illustrating the device for detecting the failure of adhesive application which is used in an adhesive application or coating device of a book-binding machine.

FIG. 8 shows the adhesive-application detection device used in the adhesive application or coating device of a book binding machine. In the adhesive-application detection device, an ultraviolet radiation source 201, a detection unit 202 and an analog-signal amplifier 203 are mounted on a supporting member 264 of the adhesive application or coating device and are interconnected with a device main body 210 through signal lines 204 and 205 and a power cord 206 so that the failure or the degree of adhesive application to a book 270 which is being transported from the book binding machine and bound, can be detected.

Figure 9:
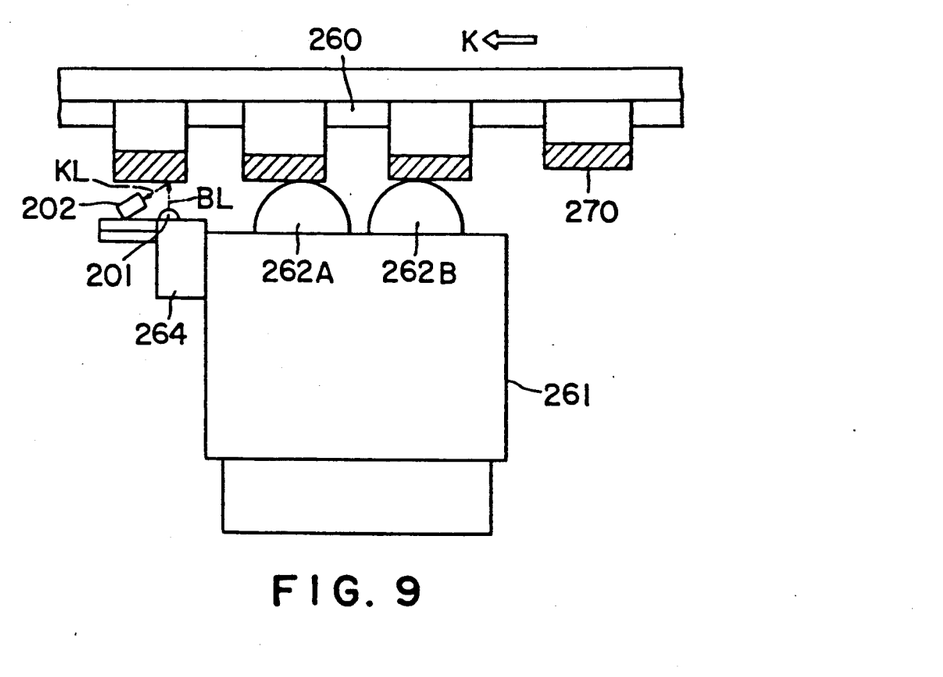
FIG. 9 is a view illustrating the positional relationship between an ultraviolet light source and a detection unit thereof.

FIG. 9 shows the positional relationships of the ultraviolet radiation source 201 and the detection unit 202 with respect to the book binding machine which will be described with reference to FIG. 8. The book binding machine is provided with an adhesive application or coating device 261 which receives and stores therein an adhesive fed through an adhesive feed pipe 263 from an adhesive tank 265 disposed below the adhesive application or coating device. When a book 270 which is in the book binding process is transported in the direction indicated by the arrow K by a transportation rail 260, adhesive application or coating rolls 262A and 262B disposed in the adhesive application or coating device 261 rotates to apply the adhesive to the spine of the book 270. The ultraviolet radiation source 201 and the detection unit 202 are disposed on the left side of the adhesive application or coating device 261 as indicated in FIG. 8 or 9 and the ultraviolet radiation source 201 projects the ultraviolet beam BL to the end face of the book 270 applied with the adhesive while the luminous emission KL from the adhesive is detected by the detection unit 202. As in the case of the above-described box-making machine, the detection unit 202 is turned on and off by a photoelectric switch and a rotary encoder.

Next, the mode of operation of the adhesive-application detection device with the above-described construction will be described. First, the adhesive-application detection device is set into the adhesive application or coating device in the book binding machine as shown in FIG. 8 and an adhesive to which a fluorescent agent has been previously added, is fed from an adhesive tank 265 into the adhesive application or coating device 261. Thereafter, the operator turns on a power switch 216 of the device main body 210 when the book binding machine is activated. The book 270 is transported along the transportation rail 260 and its spine is applied with the adhesive by adhesive application or coating rolls 262A and 262B. The fluorescent agent contained in the adhesive is excited by the ultraviolet radiation source 201 so that the luminous emission KL therefrom is detected by the detection unit 202 in the manner described above, and a lamp 218 of the operation unit 14 is turned on, indicating the satisfactory adhesive application. When the failure of the application of the adhesive to the book 270 occurs, an alarm buzzer and a lamp 219 are turned on, giving an alarm to the operator so that he/she can deactivate the book binding machine or check the book 270, etc. Furthermore, as in the above-described case, quality control of adhesive application or coating can be carried out by the display 100 of the device main body. Thereafter, the operator depresses a reset switch 217 to reset the device main body 210 to continue the operation again.

Figure 10:
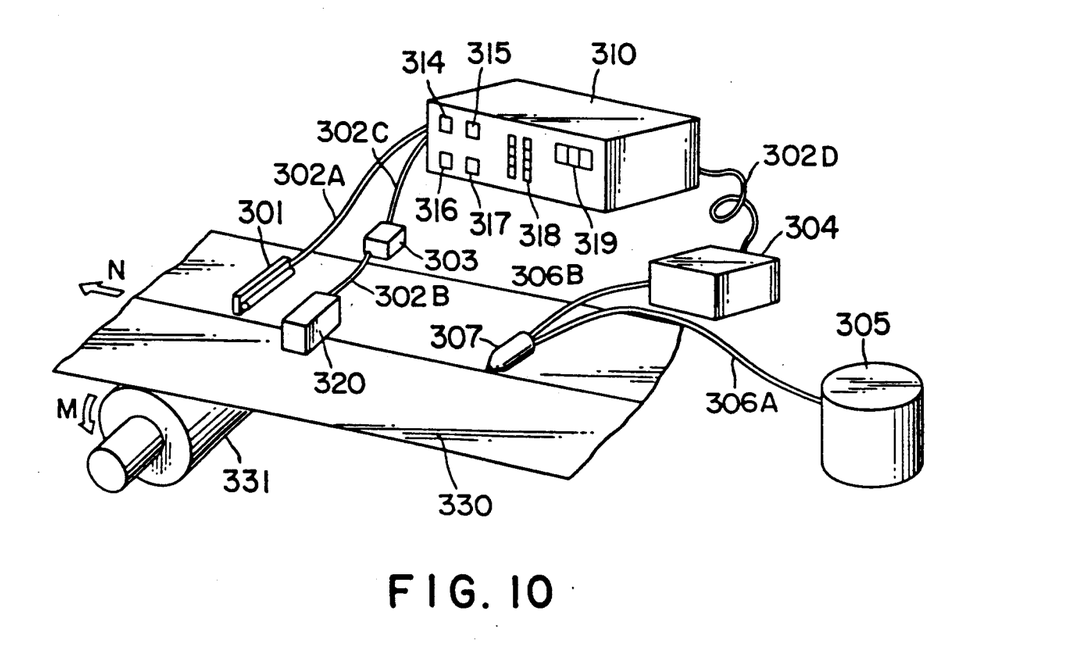
FIG. 10 is a view illustrating another embodiment of the present invention which is a device for controlling the quantity of adhesive applied, and which is used in an adhesive application or coating machine.

FIG. 10 shows an adhesive-application-quantity control device which is an embodiment of the present invention and which is used in an adhesive application or coating machine. The adhesive-application-quantity control device comprises a light source 301, a detection unit 320, an analog-signal amplifier 303, a unit for detecting the quantity of adhesive applied comprising a device main body 310 and an adhesive application or coating unit comprising an adhesive tank 305, a photoelectric conversion device 304 and an adhesive issuing nozzle 307. These units are interconnected with each other via signal lines 302A–302D and pipes 306A and 306B and a roller 331, which rotates (in the direction indicated by the arrow M), and applies a predetermined quantity of the adhesive to a predetermined position of a sheet 330 such as a continuous sheet or a continuous sheet of film or the like. The front panel of the device main body 310 has a power switch 316, a reset switch 317, a control-start switch 314, a switch 315 for the input of a reference value, a level meter 318 and a digital input switch 319.

Figure 11:
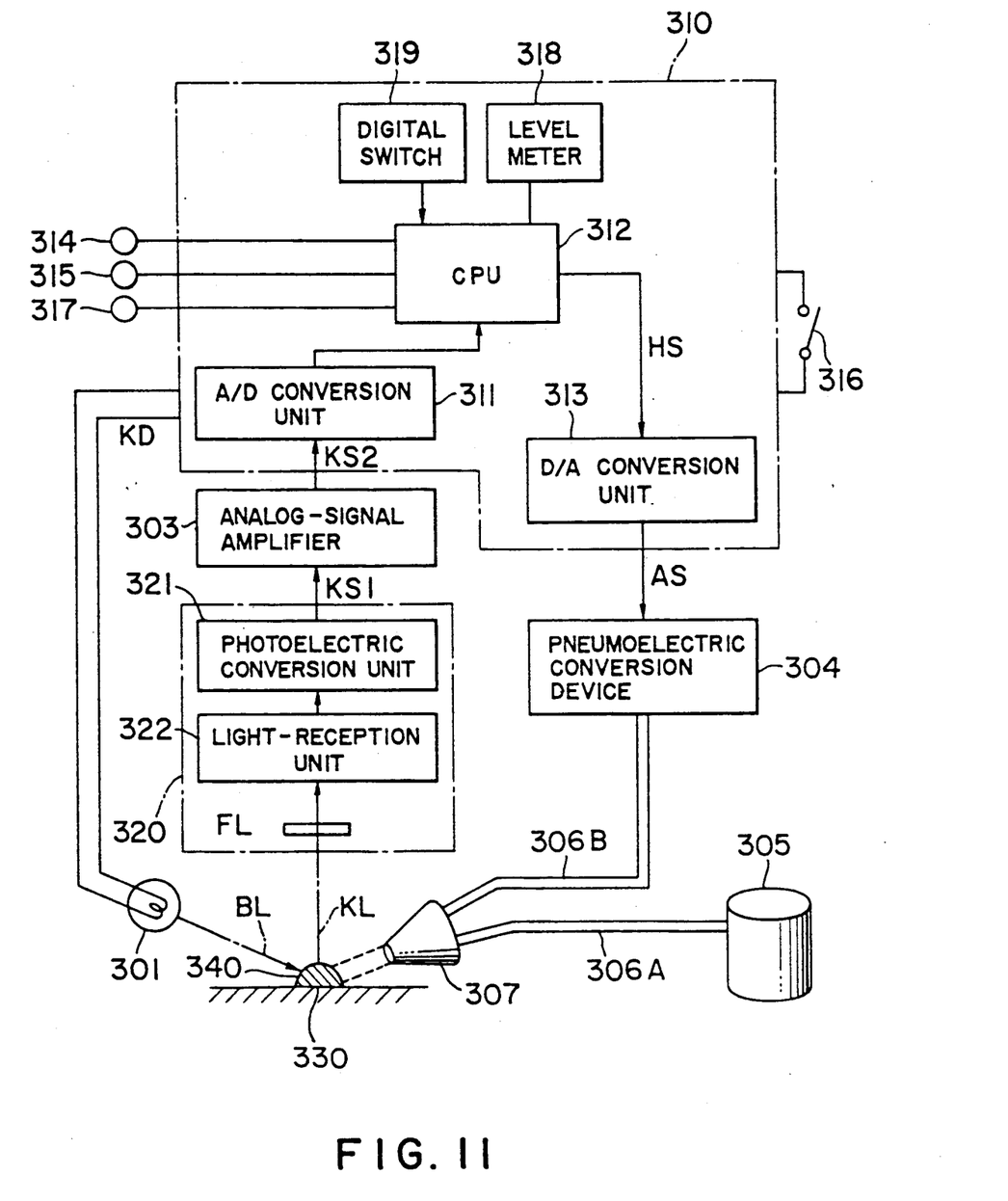
FIG. 11 is a block diagram illustrating the construction of the circuit system thereof.

FIG. 11 is a block diagram showing a circuit system of an adhesive-application-quantity control device which will be described in detail below.

(1) Light-Emission Unit 1

A fluorescent lamp type of black light or the like is used as the light-emission unit 301 which projects the ultraviolet beam B1 to an adhesive 340 (to which a fluorescent agent has been previously added), coated to a sheet 330 or the like which is being transported. In order to maintain a uniform intensity of the projected ultraviolet beam in terms of time and to stabilize the luminous emission from the adhesive 340, the high-frequency power KD (in the order of 20 KHz) is fed from a device main body 310 to turn on the fluorescent lamp type black light at a high frequency. The light-reception face of the detection unit 320 is arranged so as to make an angle of 45° with respect to the light-emission unit 301 so that the incidence efficiency of the ultraviolet beam BL which is emitted from the light-emission unit 301 and which is directly incident to the light reception face of the detection unit can be decreased and the S/N ratio can be improved.

(2) Detection Unit 320

The detection unit 320 comprises a light-reception unit 321 comprising an optical system such as a lens for efficiently receiving the luminous emission KL from the adhesive 340 and converging it to a photoelectric conversion unit 321 and the photoelectric conversion unit 321 utilizing a photodiode having a measuring wavelength range corresponding to visible light so that the luminous emission KL from the adhesive which is collected by the light reception unit 322, is received and is then subjected to photoelectric conversion. A photodiode having the characteristic of a wide measuring field of view is used, and this measuring field of view can be determined in a simple manner by the shape or the lens system of the light reception unit 322. Furthermore, only the luminous emission KL from the adhesive 340 is selectively received. In this case, in order to reduce the adverse effect of the external light rays on the signal to a minimum, a filter FL can be disposed in front of the light reception unit 322. In order to distinguish between paper and an adhesive, two detection units 320 can be used.

(3) Analog-Signal Amplifier 303

The analog-signal amplifier 303 comprises two operational amplifiers such as MOS type operational amplifiers, and is adapted to input the detection signal KS1 obtained in response to the reception of light and the photoelectric conversion of the received light by the detection unit 302 into the succeeding circuit stage after the signal is so modified or otherwise processed so as to be easily detected and the S/N ratio is improved.

(4) Device Main Body 310

(a) Decision Unit (1) A/D Conversion Unit 311

The A/D conversion unit 311 comprises a timing pulse control circuit, a clock generator, a sample-and-hold circuit, an A/D converter and so on. The detection signal K2 from the analog-signal amplifier 303 is sampled and converted into the digital signal which in turn is inputted into a CPU 312 comprising a one-board control computer. The above-described timing pulse control circuit determines the time required for the A/D conversion by input to the A/D conversion circuit of a clock pulse which has a predetermined frequency and is generated by the clock pulse generator for controlling the timing of the operation of the sample-and-hold circuit and the A/D conversion circuit in response to the control pulse from CPU 312. In order to eliminate conversion error during A/D conversion, the sample-and-hold circuit samples the analog voltage during the A/D conversion and maintains it at a data value at this moment. Sampling is carried out at a frequency of from 1 to 10 KHz. A commercially available 8- or 10-bit sequential conversion type A/D conversion IC or the like is used as the A/D conversion circuit and its input side is adapted to the bipolar input so that the range of the input signal can be widened, and consequently, construction of the entire circuit can be simplified while the output side incorporates buffers for individual bits, thereby countering noise.

(2) CPU 312

CPU 312 comprises a central processing unit (CPU) comprising a one-board computer not shown, storage devices (RAM, EPROM), an input-output interface (PPI), a decoder, a timer and so on. The intensity of the signal representative of a product to be rejected is determined from two values of the intensity of the signal representative of the application of adhesive in a predetermined quantity and the intensity of the signal representative of the application of adhesive not in a predetermined quantity. The value thus determined is stored in a storage device as a decision value. Thereafter, the values of the signals which are sequentially read out of the input-output interface are compared with the decision value stored in the storage device by the CPU, thereby determining the quantity of the adhesive applied. When the quantity of the adhesive applied is detected as being insufficient, the CPU computes the digital signal HS for controlling the quantity of the adhesive applied and inputs it through the input-output interface into a D/A conversion unit 313. Furthermore, a (digital) value corresponding to a quantity of the adhesive applied is stored previously in a storage device through a reference-value input switch 315 and a digital switch 319 and the readout input signal is detected in the manner described above and the control signal HS for controlling the quantity of the adhesive applied is output while being sequentially displayed by a level meter 318. A reset switch 317 and a control-start switch 314 are further provided and when the operator uses the device for controlling the quantity of the adhesive applied, he/she turns on the power switch 316 and sets the quantity of the adhesive to be applied by the digital input switch 319 and inputs it by the reference-value input switch 315. Thereafter, the operator depresses the control-start switch 314, thereby activating the device. When it is desired to change the set value of the quantity of the adhesive to be applied, the operator depresses the reset switch 17 to repeat the above-described operation, thereby performing the input of new data.

(b) D/A Conversion Unit 313

The D/A conversion unit 313 converts the control signal for controlling the quantity of the adhesive to be applied which is input by CPU 312, into the analog control signal AS, which in turn is input into the pneumoelectric conversion device 304.

(5) Adhesive Application or Coating Unit (a) pneumoelectric Conversion Device 304

In response to the control signal AS from the device main body 310, the pneumoelectric conversion 304 applies the air pressure to the adhesive being fed through the pipe 306A from the adhesive tank 305, thereby issuing a predetermined quantity of the adhesive through the nozzle 307 to the sheet or the like 330.

Figure 12:
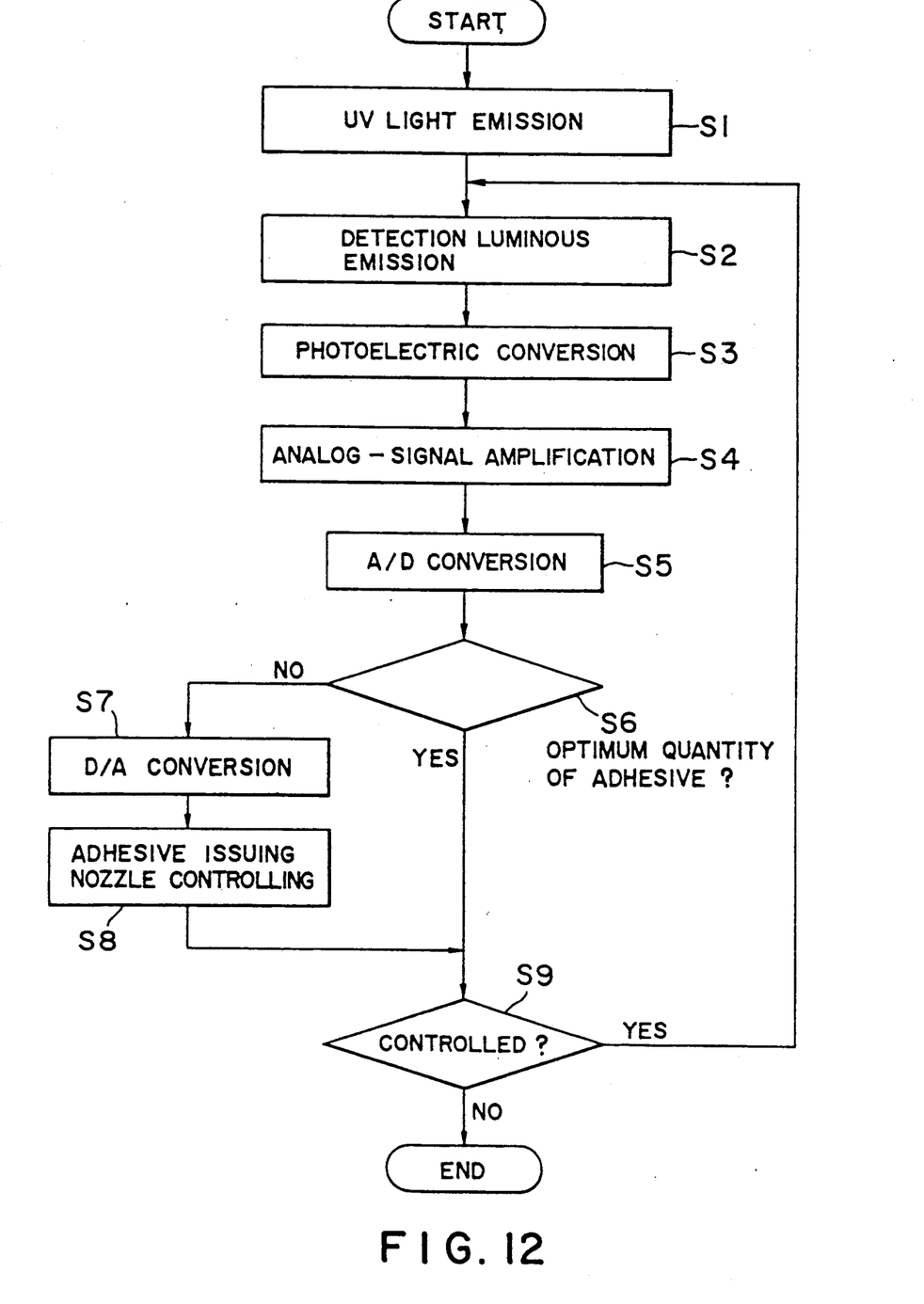
FIG. 12 is a flowchart used to explain the mode of operation thereof.

Next referring to the flowchart shown in FIG. 12, the mode of operation of the device for controlling the quantity of application of the adhesive which is used in the adhesive application or coating machine will be described.

First, the device for controlling the quantity of the adhesive to be applied is set into the adhesive application or coating machine as shown in FIG. 10 and the adhesive 340 to which a fluorescent agent has been added beforehand, is supplied into the adhesive tank 305. Thereafter, the operator depresses the power switch 316 of the device main body 310 to activate the adhesive application or coating machine, thereby setting the quantity of the adhesive to be applied to a value predetermined by the digital input switch 319, and then depresses the reference-value input switch 315. Next, when the operator turns on the control-start switch 314, the black light in the light-emission unit 301 is turned on (step: S1) and the device for controlling the quantity of the adhesive to be applied is activated. The adhesive 340 is issued through the adhesive issuing nozzle 307 and is applied to a predetermined position on the sheet or the like 330. The luminous emission KL from the adhesive 340 excited by the ultraviolet beam from the light-emission source 301 is detected by the detection unit 320 (step: S2) and is subjected through the light-reception unit 322 to photoelectric conversion by the photoelectric conversion unit 321 in the detection unit 320 (step: S3). The detection signal KS is amplified by the analog-signal amplifier 303 (step: S4) and is input as the detection signal KS2 into the device main body 310 to be subjected to the A/D conversion by the A/D conversion unit 311 (step: S5) and then input to CPU312. CPU312 compares the set value input by the above-described digital input switch 319 with the digital signal input from the above-described A/D conversion unit to compute an optimum quantity of the adhesive to be applied. When the input digital signal is different from the set value (step: S6), a new signal HS for controlling the quantity of the adhesive to be applied is output, and input to the D/A conversion unit 313 for carrying out the D/A conversion (step: S7). The control signal HS is input to the photoelectric conversion device 304 and the quantity of the adhesive 340 discharged from the adhesive issuing nozzle 307 is controlled (step: S8). When the quantity of the adhesive applied is satisfactory, the signal HS for controlling the quantity of the adhesive to be applied, remains at the initially set value so that the quantity of the adhesive to be applied is maintained at a predetermined value (steps: S6, S9 and S2).

When it is desired to change the quantity of the adhesive to be applied, the operator depresses the reset switch 317 once to reset the device main body 310, resets the quantity of the adhesive to be applied and then depresses the control-start switch 314, thereby activating the device. In the device for controlling the quantity of the adhesive to be applied, the quantity of the adhesive is displayed by the level meter 318 so that quality control in the adhesive application process can be easily attained in response to the check of the quantity of the adhesive applied by the operator.

The quantity of a fluorescent agent contained in an adhesive is determined in such a way that a 1-5% aqueous solution of the fluorescent agent is contained at the ratio of from 0.3 to 10% and in this embodiment a 4% aqueous solution is contained at the ratio of 1%. In the above-described embodiment, a one-board computer is used as the control computer in CPU312 of the device main body 310, but it is to be understood that a personal computer can be also used. The control arithmetic circuit or the like is used in the embodiment in order to carry out the method for executing the subtraction process of the input signal, but it is to be understood that an output difference can be computed according to a previously incorporated computer program. In addition, when a plurality of detection units 320 are decided by the one judgment unit, a multiplexer circuit can be incorporated into the judgment unit so that the detection signals are sequentially compared. Furthermore, in this embodiment, the method for optically detecting the luminous emission from a fluorescent agent is employed, but it is to be understood that any other conventional detection means such as a method for detecting the electrostatic capacitance or the like can be used. The nozzle system is used as an adhesive application or coating means, but it is to be understood that any other adhesive application or coating means such as a ball-point-pen system or the like can be used. In addition, the photoelectric conversion device is used as means for controlling the quantity of the adhesive to be applied in the embodiment, but it is to be understood that the quantity of the adhesive can be controlled by varying the degree of opening of a nozzle.

INDUSTRIAL APPLICABILITY

A method and device in accordance with the present invention for detecting objects to be detected in response to the luminous emission from a fluorescent substance can be utilized to inspect whether or not the failure of adhesive application occurs or the degree of adhesive application in the adhesive application or coating step carried out by the collator, the box-making machine, the book-binding machine or the like.

What is claimed is:

1. A method of detecting a streak formed on an article, having printing thereon the streak comprising a fluorescent substance, the method comprising the steps of:

projecting an ultraviolet beam to the streak;
detecting a luminous emission of the fluorescent substance and external disturbance light rays from a surface of the article using two or more light reception elements that have means for setting the measurement field of view; and
executing a subtraction process between a value of an output of each of said light reception elements, thereby detecting the streak despite said external disturbance light rays.

2. A method of detecting a streak formed on an article, having printing thereon the streak comprising a fluorescent substance, the method comprising the steps of:

projecting an ultraviolet beam to the streak;
measuring an intensity of said ultraviolet beam;
detecting a luminous emission signal of the fluorescent substance and external disturbance light rays from a surface of the article using two or more light reception elements;
executing a division and a substraction process between a value of an output of each of said light reception elements, wherein said luminous emission signal is divided by said measured intensity of said ultraviolet beam to attain a normalized value; and
comparing said normalized value with a previously input reference value, thereby detecting the streak despite said external disturbance light rays.

3. An adhesive-application detection method for detecting a failure or determining a degree of adhesive application of a streak of a fluorescent adhesive automatically applied to an article having printing thereon and being transported, the method comprising the steps of:

projecting an ultraviolet beam to the adhesive when the adhesive is applied to the article; and detecting a quantity of luminous emission and external disturbance light rays from the article using two or more light reception elements that have means for setting the measurement field of view, thereby determining the failure or the degree of adhesive application.

4. An adhesive-application detection device for detecting a streak of an adhesive comprising a fluorescent substance, the streak being automatically applied to an article having printing thereon and being transported, the adhesive-application detection device comprising:

light source means for projecting an ultraviolet beam to the adhesive when the adhesive is applied to the article;

detection means for detecting a quantity of a luminous emission from the adhesive excited by said light source means and a quantity of external disturbance light rays from the surface of the article by light reception elements that have means for setting the measurement field of view; and adhesive-application detection means for detecting a failure or degree of adhesive application in response to a detection signal from said detection means, said adhesive application detection means activating an alarm when said failure of adhesive application occurs with respect to a predetermined condition.

5. The adhesive-application detection device of claim 4, said detection means further comprising a detection unit which converts said luminous emission and said external disturbance light rays into an electrical signal and processes said electrical signal, thereby transmitting said electrical signal through a signal line to a device main body.

6. The adhesive-application detection device of claim 4, said adhesive application detection means further comprising a timing pulse control circuit, a clock generator, a sample-and-hold circuit, an A/D conversion unit comprising an A/D conversion circuit, a control computer and an alarm device, whereby said detection signal is compared with a decision value stored in storage means in said control computer to activate said alarm device when said failure of adhesive application occurs.

7. The adhesive-application detection device of claim 5, said detection unit further comprising photoelectric conversion elements each having a measuring wavelength range corresponding to visible light, whereby said luminous emission and said external disturbance light rays are received and converted into electrical signals by photoelectric conversion.

8. An adhesive-application control device for controlling a quantity of adhesive to be applied to an article being transported, the adhesive comprising a fluorescent substance, the adhesive-application control device comprising:

light source means for projecting an ultraviolet beam to the adhesive when the adhesive is applied to the article;

detection means for detecting a quantity of a luminous emission from the adhesive when the fluorescent substance thereof is excited by said light source means using light reception elements;

control means for detecting a quantity of the adhesive applied to the article in response to a detection signal from said detection means and for sequential output of control data for controlling the quantity of adhesive to be applied; and adhesive-application means for applying the adhesive to the article based upon said control data.

9. The adhesive-application control device of claim 8, said control means further comprising an optimum-adhesive-application-quantity presetting system which utilizes adhesive-quantity control data for individual items.

10. The adhesive-application control device of claim 8, said control means further comprising a light emission unit, a detection unit, an analog-signal amplifier and a unit for detecting the quantity of the adhesive applied which comprises a device main body and an adhesive-application unit interconnected to said device main body through signal lines and pipes, said adhesive-application unit comprising an adhesive tank, a pneumoelectric conversion device and an adhesive issuing nozzle;

whereby the adhesive is uniformly applied to the article of a continuous sheet of paper or film, the article being transported by rotating rollers in response to said control data output from said control means for controlling the quantity of the adhesive to be applied.

* * * * *